United States Patent
Xu et al.

(10) Patent No.: US 7,110,238 B1
(45) Date of Patent: Sep. 19, 2006

(54) SYSTEMS AND METHODS FOR USING NON-CONTACT VOLTAGE SENSORS AND CORONA DISCHARGE GUNS

(75) Inventors: Zhiwei (Steve) Xu, Sunnyvale, CA (US); Jianou Shi, Milpitas, CA (US); Shiyou Pei, Campbell, CA (US); Mahmood Mirzaaghaeian, Fremont, CA (US); Jeffrey A. Rzepiela, Sunnyvale, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 0 days.

(21) Appl. No.: 11/154,991

(22) Filed: Jun. 16, 2005

Related U.S. Application Data

(62) Division of application No. 10/606,066, filed on Jun. 24, 2003, now Pat. No. 6,909,291.

(51) Int. Cl.
*H01H 47/00* (2006.01)
(52) U.S. Cl. .................................................... 361/220
(58) Field of Classification Search ................. 361/220
See application file for complete search history.

(56) References Cited

U.S. PATENT DOCUMENTS

| | | | |
|---|---|---|---|
| 4,599,558 A | 7/1986 | Castellano, Jr. et al. | 324/752 |
| 4,812,756 A | 3/1989 | Curtis et al. | 324/750 |
| 4,973,910 A | 11/1990 | Wilson | 324/457 |
| 5,136,247 A | 8/1992 | Hansen | 324/457 |
| 5,485,091 A | 1/1996 | Verkuil | 324/455 |
| 5,594,247 A | 1/1997 | Verkuil et al. | 250/326 |
| 5,644,223 A * | 7/1997 | Verkuil | 324/158.1 |
| 5,650,731 A | 7/1997 | Fung et al. | 324/752 |
| 5,767,693 A | 6/1998 | Verkuil | 324/767 |
| 5,963,783 A | 10/1999 | Lowell et al. | 438/17 |
| 6,011,404 A | 1/2000 | Ma et al. | 324/765 |
| 6,060,709 A | 5/2000 | Verkuil et al. | 250/326 |
| 6,097,196 A | 8/2000 | Verkuil et al. | 324/750 |
| 6,138,054 A | 10/2000 | On | 700/121 |
| 6,202,029 B1 | 3/2001 | Verkuil et al. | 702/64 |
| 6,717,413 B1 | 4/2004 | Danyluk et al. | 324/459 |
| 6,909,291 B1 * | 6/2005 | Xu et al. | 324/601 |

OTHER PUBLICATIONS

Yoshitake et al., "Measurement of work function change with surface segregation of substrate element on a deposited film," May 1999, Applied Surface Science, vol. 1467, issues 1-4, pp. 97-100.
Schroder, "Surface voltage and surface photovoltage: history, theory and applications," Measurement Science and Technology, vol. 12, 2001, pp. R16-31.

* cited by examiner

*Primary Examiner*—Stephen W. Jackson
(74) *Attorney, Agent, or Firm*—Ann Marie Mewherter; Daffer McDaniel, LLP

(57) ABSTRACT

A method and a system for calibrating the work function of a non-contact voltage sensor are provided. The method includes preparing a reference sample to have a stable work function, measuring a voltage of the sample using a non-contact voltage sensor, and determining a work function correction factor of the sensor from the measured voltage. In turn, the calibrated work function may be used to adjust voltages of substrates measured by the sensor. A corona gun which includes a first electrode and one or more conductive rods is provided. In some embodiments, the conductive rods may be angled between 0 and 90 degrees with respect to a first electrode sidewall and/or be concentrically arranged less than 90 degrees from each other. In addition or alternatively, the corona gun may be adapted to alter its length and/or include a second electrode partially inset within a space surrounded by the first electrode.

24 Claims, 3 Drawing Sheets

SYSTEMS AND METHODS FOR USING NON-CONTACT VOLTAGE SENSORS AND CORONA DISCHARGE GUNS

PRIOR APPLICATION

This application is a divisional application from prior application Ser. No. 10/606,066 filed Jun. 24, 2003 now U.S. Pat. No. 6,909,291.

BACKGROUND OF THE INVENTION

1. Field of the Invention

This invention generally relates to microelectronic device manufacturing and, more specifically, to methods and systems for measuring a voltage of a microelectronic topography.

2. Description of the Related Art

Inaccurate analysis of one or more parameters within a microelectronic device, such as a transistor, may hinder or prohibit the function of the device, leading to a reduction in production efficiency and device quality. The characterization of thin films is especially important, since the effectiveness and reliability of thin films play an important, central role in the operation of a microelectronic device. The term "thin film" is commonly used within the microelectronic industry when referring to layers deposited upon a wafer during the fabrication of a microelectronic device. Thin film materials may include, but are not limited to, metallic, semiconductor, and dielectric materials or a combination of such materials. Often, thin films are doped with impurities to heighten the effectiveness of the material used. In order for a thin film to be effective, it must conform to strict electrical, chemical, and structural requirements. Therefore, thin films must be accurately analyzed in order to meet a microelectronic device's functionality requirements. In addition, as production volumes and efforts to improve process control increase in the integrated circuit fabrication industry, the ability to accurately characterize microelectronic processes and the materials associated with such processes in a timely manner becomes more critical.

A thin film may be characterized by a number of different properties. For example, a thin film may be characterized by its composition, physical thickness, and/or electrical properties, to name just a few. Consequently, a number of different techniques may be used to characterize a thin film. For example, electrical test techniques may provide electrical capacitance, electrical thickness, and electrical conductivity information about thin films. It is a significant advantage to be able to directly measure electrical properties of a material since the end-usage of microelectronic products is electrical in nature. In some cases, non-contacting systems may be used for such measurements, providing electrical information without having an electrode physically contact a thin film. In this manner, damage to the microelectronic topography may be prevented.

Non-contact techniques typically use an ion generation source such as a corona to source, and a non-contacting voltage measurement sensor such as a Kelvin probe, a Monroe probe, or an atomic force microscope probe, to determine electrical properties of the films. Examples of such systems are illustrated and/or described in U.S. Pat. No. 5,485,091 to Verkuil, U.S. Pat. No. 5,594,247 to Verkuil et al., U.S. Pat. No. 6,097,196 to Verkuil et al., and U.S. Pat. No. 6,202,029 B1 to Verkuil et al., which are incorporated by reference as if fully set forth herein. In order to provide highly accurate results, it is generally advantageous to control corona charge deposition to a high level of precision and uniformity. Conventional techniques that are able to deposit uniform charges, however, usually suffer from a low deposition rate. As such, there is typically a trade-off between uniformity and deposition rate when using non-contact electrical testing techniques.

Another difficulty with non-contacting testing systems is that the measured voltage includes contributions not just from the surface to be measured, but also from the work function of the surface being measured and the work function of the sensor used for the measurement. In general, any non-contacting voltage measurement between a probe and a sensor will result in a measured voltage of:

$$V_{measured} = V_{probe\_surface} + \phi_{ms}$$

where $V_{measured}$ is the measured voltage, $V_{probe\_surface}$ is the desired voltage to be measured, and $\phi_{ms}$ is the work function difference between the probe and measured surface. In ambient conditions, $\phi_{ms}$ is difficult to determine and is a function of not only the material properties of the sensor and measured surface, but of ambient conditions such as temperature, humidity, water layers on the measured surface, partial pressures of various trace gases in the air, and air-borne molecular contamination. $\phi_{ms}$ is also known to drift over extended periods of time. For example, practical measurements of the stability of $\phi_{ms}$ show that it is difficult to prevent drifts on the order of greater than about 10 mV over timescales of hours or several hundred mV over a longer time period. Therefore, uncertainty in $\phi_{ms}$ adds uncertainty to the measured voltage.

The work function of a sensor may have a particularly strong influence on such measurement variations since the sensor is used for multiple measurements. The exposure of the substrates to be measured, on the other hand, is limited and is usually consistent since they are measured at the same point in the fabrication process. In any case, in an effort to overcome the problems associated with ambient environments, non-contact electrical testing techniques are sometimes conducted in an ultra-high vacuum environment. Unfortunately, however, an ultra-high vacuum environment is typically costly and difficult to maintain, making the use of such an environment impractical for many applications.

As such, it would be advantageous to develop a system and a method for calibrating the work function of a non-contact voltage sensor such that electrical properties of a thin film may be measured in an ambient environment. In addition, it would be advantageous to develop a corona discharge gun that deposits corona in an efficient and uniform manner.

SUMMARY OF THE INVENTION

The problems outlined above may be in large part addressed by a method for calibrating the work function of a non-contact voltage sensor. In particular, the method may include preparing a reference sample to have a substantially stable work function, measuring a voltage of the reference sample using a non-contact voltage sensor, and determining a work function correction factor of the non-contact voltage sensor from the measured voltage. In some embodiments, the step of determining the work function correction factor may involve determining a difference between the measured reference sample voltage and a previously measured voltage of the reference sample. More specifically, the step of determining the work function correction factor may involve determining a work function variance between the measured reference sample voltage and a previous voltage measurement of the reference sample. In yet other embodiments, the step of determining the work function correction factor may involve calculating the work function of the non-contact voltage sensor from a known work function of the reference sample and preset voltage values of the reference sample and the non-contact voltage sensor.

In either case, the step of preparing the reference sample may include controlling an environment around the reference sample and/or treating the reference sample. In particular, the step of preparing the reference sample may, in some embodiments, include stripping a surface of the reference sample or depositing a layer upon the reference sample prior to the step of measuring a voltage of the reference sample. In yet other embodiments, the step of preparing the reference sample may include controlling the environment around the reference sample prior to and, in some embodiments, subsequent to measuring a voltage of the reference sample. For example, in some cases, the step of preparing the reference sample may include storing the reference sample in an isolated area, such as a chamber. In addition or alternatively, the step of preparing the reference sample may include illuminating the reference sample.

In some embodiments, the environment around the reference sample may be additionally or alternatively controlled by purging an area around the reference sample with an inert gas. Such a step of purging may include purging the area at time intervals between approximately 0.001 seconds and approximately 1 hour at a frequency between approximately 0.0001 Hz and approximately 1 KHz. Other time intervals and frequencies for purging air around the reference sample, however, may also be used. In some embodiments, the step of controlling the environment around the reference sample may include inducing a vacuum about the reference sample. In addition or alternatively, the step of controlling the environment around the reference sample may, in some cases, include maintaining the controlled environment at a temperature between approximately 20° C. and approximately 1000° C. for a time period between approximately 1 second and approximately 1 hour. In any case, the method may, in some embodiments, include removing the reference sample from the controlled environment prior to measuring the reference sample voltage and returning the reference sample to the controlled environment subsequent to the step of measuring the reference sample voltage. In yet other embodiments, the method may include terminating the exposure of the one or more environmental parameters to the isolated area around the reference sample.

A method of using a non-contact voltage sensor system is also contemplated herein. In particular, the method may include calibrating the work function of a non-contact voltage sensor and adjusting a measured voltage of a substrate based upon the calibrated work function. In some embodiments, the step of adjusting the measured substrate voltage may include subtracting the calibrated work function from the measured substrate voltage. In other embodiments, the step of adjusting the measured substrate voltage may include reconfiguring the non-contact voltage sensor to automatically accommodate the work function correction factor that was determined in the calibration step. In either case, the step of adjusting may generally include adjusting a surface voltage measurement, a flatband voltage measurement, or a tunneling voltage measurement of the substrate. In some cases, the measured substrate voltage may be obtained subsequent to the step of calibrating. In yet other embodiments, however, the measured substrate voltage may be obtained prior to the step of calibrating. In either case, the method may further include repeating the step of calibrating after measuring a subset of a plurality of samples. In some cases, the step of repeating may be conducted between each voltage measurement of the plurality of samples.

Consequently, a system for determining an electrical parameter of a substrate is provided herein. In general, the system may include a non-contact voltage sensor, such as a Kelvin probe, a Monroe probe, or an atomic force microscope probe, for example. In addition, the system may include a substrate holder and an area isolated from the substrate holder which is adapted to prepare a reference sample to have a substantially stable work function. In some cases, the system may further include a stage having the substrate holder arranged thereon. In some embodiments, the isolated area may be arranged on the stage adjacent to the substrate holder. In yet other embodiments, however, the isolated area may not be arranged upon the stage.

A corona discharge system is also provided herein. In general, the corona discharge system may include a first beam shaping electrode and one or more conductive rods extending into a space surrounded by the first beam shaping electrode. The conductive rods may be biased to a relatively high voltage source during operation of the corona gun such that the conductive rods may serve as a corona excitation source. In some embodiments, the one or more conductive rods may be arranged at an angle between approximately 0 degrees and approximately 90 degrees with respect to a sidewall of the first beam shaping electrode. In addition or alternatively, the one or more conductive rods may, in some cases, be concentrically spaced from each other by less than approximately 90 degrees. In such an embodiment, the one or more conductive rods may include a plurality of needles. In yet other cases, the one or more conductive rods may additionally or alternatively include a plurality of wires extending between sidewalls of the first beam shaping electrode. Such a plurality of wires may generally be arranged parallel to each other and spaced apart by an amount between approximately 1 mm and approximately 5 mm. In any case, the corona gun described herein may generally include any number of conductive rods. For example, the corona gun described herein may include between one and eight conductive rods in some embodiments. In other cases, however, the corona gun provided herein may include more than eight conductive rods.

In some cases, the corona discharge system may include one or more additional beam shaping electrodes. In particular, the corona discharge gun may, in some embodiments, include a second beam shaping electrode spaced adjacent to the first beam shaping electrode. In addition, the corona discharge gun may, in some embodiments, include a third beam shaping electrode spaced adjacent to the second beam shaping electrode. In general, at least one of the second and third beam shaping electrodes may include an opening having a width between approximately 5 microns and approximately 4 cm. In some embodiments, at least one of the second and third beam shaping electrodes may include a tapered opening. In addition or alternatively, the portions of at least one of the second and third beam shaping electrodes forming the lateral boundaries of their respective openings may be rounded. In yet other embodiments, the portions of the second and third beam shaping electrodes forming the lateral boundaries of their respective openings may have a substantially straight and vertical profile.

In some cases, a portion of the second beam shaping electrode may overlap a portion of the first beam shaping electrode. For example, in some embodiments, the second beam shaping electrode may be at least partially inset within a space surrounded by the first beam shaping electrode. In particular, the second beam shaping electrode may be inset at least approximately 0.1 inches into the space surrounded by the first beam shaping electrode. In some cases, a portion of the second beam shaping electrode inset within the space surrounded by the first beam shaping electrode may be configured to surround a space having a width which is approximately 0.2 inches to approximately 1.0 inch smaller than a width of the space surrounded by the first beam shaping electrode. In yet other embodiments, the first beam shaping electrode may be least partially inset within a space surrounded by the second beam shaping electrode.

In some embodiments, the corona discharge system may be adapted to alter the length of the corona gun or, more specifically, the distance between a corona a excitation source and an opening of one of the beam shaping electrodes. For example, in some embodiments, one or more of the beam shaping electrodes may be adapted to contract and expand. More specifically, one or more of the beam shaping electrodes may include telescoped sidewalls. In addition or alternatively, one or more of the beam shaping electrodes may include accordion-style sidewalls. In yet other embodiments, at least one of the beam shaping electrodes may be additionally or alternatively adapted to move relative to another of the beam shaping electrodes. In any case, the corona discharge gun to may be further configured to move the corona excitation source relative to an opening of one of the beam shaping electrodes.

There may be several advantages to using the systems and methods provided herein. For example, more accurate voltage measurements of substrates may be obtained due to the method and system presented fior calibrating the work function of a non-contact voltage sensor. As a result, more accurate values pertaining to electrical properties of the substrate may be obtained. Moreover, the methods and systems provided herein offer a manner with which to measure a voltage of a substrate using a non-contact voltage sensor in an ambient environment. Consequently, the use of ultra-high vacuums may be avoided. In addition, corona ions may be deposited in a more uniform and efficient manner with the corona gun configurations described herein. Furthermore, the length of a corona gun may be customized for individual operations, using the provided adaptations to alter the length of the corona gun.

BRIEF DESCRIPTION OF THE DRAWINGS

Other objects and advantages of the invention will become apparent upon reading the following detailed description and upon reference to the accompanying drawings in which:

FIG. 4b depicts a top view of the corona gun taken along line AA in FIG. 4a;

FIG. 5b depicts a top view of the corona gun in the alternative embodiment taken along line BB in FIG. 5a.

Figure 1:
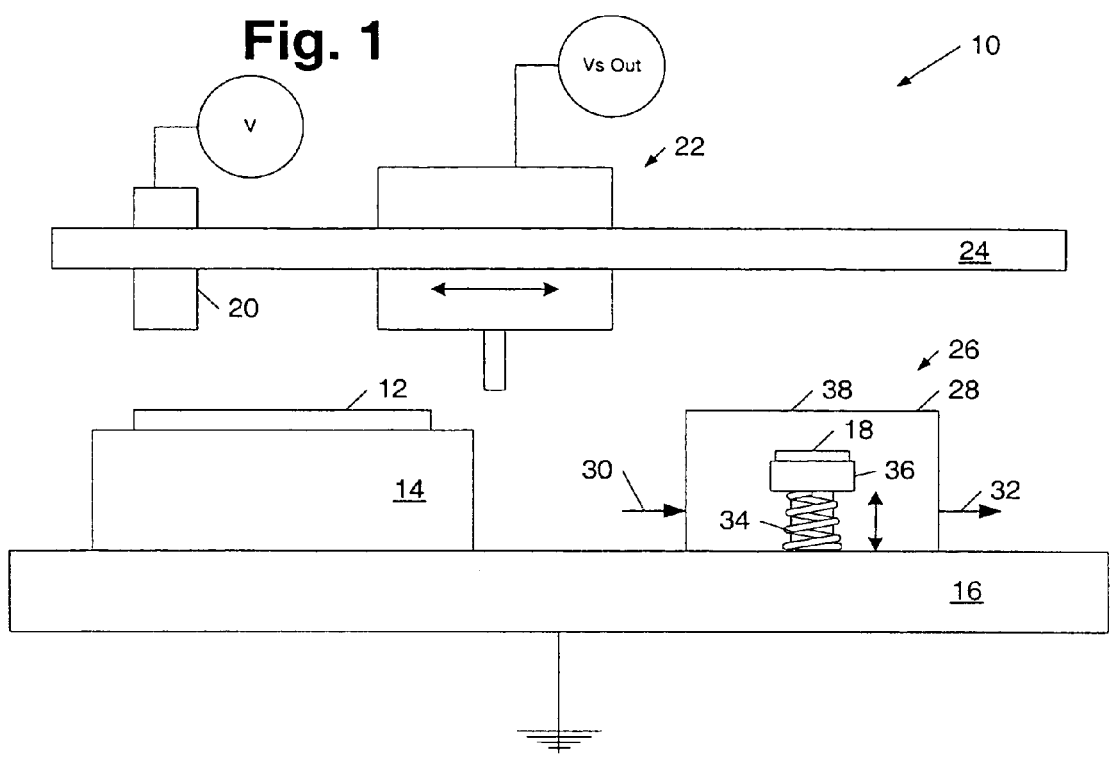
FIG. 1 depicts a partial cross-sectional view of a non-contact voltage sensor system.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

Turning now to the drawings, exemplary embodiments of systems and methods for determining properties of a wafer using non-contact electrical testing techniques as well as different configurations of corona discharge guns are illustrated in FIGS. 1–6. More specifically, FIG. 1 illustrates an exemplary embodiment of a system that employs non-contact electrical testing techniques for determining properties of a microelectronic topography, while FIGS. 2 and 3 outline methods of using such a system. In addition, FIGS. 4a–6 illustrate exemplary configurations of a device used to deposit corona charge upon a topography for electrical testing. It is noted that the systems and methods illustrated and described in reference to FIGS. 1–6 are not co-dependent and, therefore, may not necessarily be employed together.

An example of a system configured to measure charge density and voltage using non-contacting techniques is illustrated in FIG. 1. In particular, system 10 is shown configured to measure current-voltage characteristics of substrate 12. In a common implementation, the systems and methods described herein may be used for non-contact electrical testing of any material used for the fabrication of a microelectronic device. As such, substrate 12 may, in some embodiments, be a semiconductor substrate. In particular, substrate 12 may include doped silicon, gallium arsenide, indium phosphide, or any other substrate used in the microelectronic fabrication industry. In some cases, substrate 12 may further include one or more layers and/or structures formed upon a semiconductor substrate. Such layers and structures may include insulating and/or conductive materials.

As shown in FIG. 1, system 10 may include substrate holder 14 to support substrate 12. In addition, system 10 may include stage 16 with which to support substrate holder 14 and the components affiliated with substantially stabilizing a work function of reference sample 18, as described in more detail below. In this manner, substrate 12 and reference sample 18 may be arranged in close proximity to each other, allowing consecutive measurements of the respective substrates to be conducted within a relatively short time period. As shown in FIG. 1, stage 16 may also provide a grounding contact to substrate 12 and reference sample 18. In other embodiments, however, stage 16 may be omitted from system 10 and substrate holder 14 as well as the substrate holder used to support reference sample 18 may collectively or individually provide grounding contacts to the respective substrates. In such an embodiment, reference sample 18 may be arranged in close proximity to substrate 12 or may be arranged a substantial distance from substrate 12. In either case the components affiliated with substantially stabilizing the work function of the reference substrate may or may not be considered part of system 10 in such an embodiment. In particular, system 10 and the components affiliated with substantially stabilizing the work function of reference sample 18 may be considered elements of a single system or may be considered separate systems.

In either case, system 10 may further include corona gun 20 with which to deposit corona charged ions onto substrate 12 and reference sample 18. In general, corona gun 20 may be coupled to a relatively high voltage source, such as a source adapted to supply a voltage between approximately 6 kV and approximately 12 kV, for example. Exemplary configurations of corona discharge guns are illustrated in FIGS. 4a–6 and are described in more detail below. Additional examples of corona sources are illustrated in U.S. Pat. No. 4,599,558 to Castellano et al., U.S. Pat. No. 5,594,247 to Verkuil et al., and U.S. Pat. No. 5,644,223 to Verkuil and are incorporated by reference as if fully set forth herein. As such, system 10 is not necessarily restricted to corona discharge guns with the configurations depicted in FIGS. 4a–6. Rather, system 10 may include a corona source with any configuration. In any case, system 10 may, in some embodiments, be configured to measure the amount of charge deposited upon substrate 12. For example, system 10 may include a current-to-voltage converter to covert the current flowing through substrate 12 from corona gun 20 to a voltage. This voltage may be integrated with a charge integrator to provide a measure of the charge deposited by corona gun 20 on substrate 12.

In any case, system 10 may further include non-contact voltage sensor 22. In general, non-contact voltage sensor 22 may include any probe adapted to measure the voltage of a microelectronic topography, such as but not limited to a Kelvin probe, a Monroe probe, or an atomic force microscope (AFM) probe. Other examples of non-contact voltage sensors that may be incorporated into system 10 are illustrated in U.S. Pat. No. 4,812,756 to Curtis et al., U.S. Pat. No. 5,650,731 to Fung, and U.S. Pat. No. 5,767,693 to Verkuil, which are incorporated by reference as if fully set forth herein. In fact, system 10 may generally include any non-contact voltage sensor known for metrology of microelectronic topographies. Regardless of the type of sensor used, non-contact voltage sensor 22 may be preferably formed of a substantially inert material. For example, non-contact voltage sensor 22 may include, but is not limited to, gold, stainless steel, indium tantalum oxide (ITO), and tantalum oxide. As shown in FIG. 1, corona gun 20 and non-contact voltage sensor 22 may be coupled to sensor mount 24. In a preferred embodiment, corona gun 20 and non-contact voltage sensor 22 may be configured to move along sensor mount 24 such that the components may be positioned over sample 12 and reference sample 18.

In some cases, system 10 may further include a controller configured to control operation of the system. In particular, system 10 may include a dedicated microprocessor-based controller or a general-purpose computer to automate the operations of system 10. Consequently, the methods described herein may, in some embodiments, be computer-implemented methods. In some cases, the controller may be configured to control the position of corona gun 20 and non-contact voltage sensor 22 along sensor mount 24. In addition or alternatively, the controller may be configured to control the high voltage source coupled to corona gun 20 in response to non-contact voltage sensor 22. The controller may additionally or alternatively be configured to provide a measurement of the current-voltage behavior of substrate 12 and reference sample 18.

As noted above, system 10 may, in some embodiments, include one or more components with which to substantially stabilize the work function of a reference sample. In this manner, the work function of non-contact voltage sensor 22 may be calibrated. More specifically, a work function correction factor of non-contact voltage sensor 22 may be determined to compensate for the work function variation of the non-contact voltage sensor. As noted above, non-contact voltage sensors may experience work function variation when operated in a non-vacuum environment. In particular, air-borne contaminants within an ambient environment may adsorb onto a non-contact voltage sensor, causing the work function of the sensor to vary. In some embodiments, the work function variation of a non-contact voltage sensor may be significant, skewing the voltage measurements taken by the sensor. Since the method and system described herein allows the work function of the non-contact voltage sensor to be calibrated, however, the voltage measurements taken by such a sensor may be more accurate than measurements taken from a non-contact voltage sensor which is not calibrated. As a result, voltage measurements of substrates, such as substrate 12, for example, may be more accurate.

Figure 2:
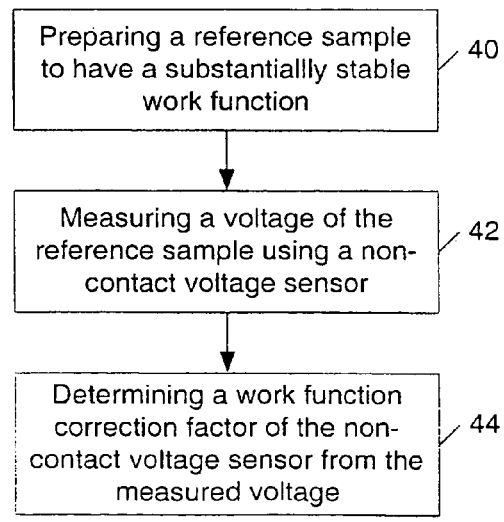
FIG. 2 depicts a flowchart of a method for calibrating a work function of a non-contact voltage sensor.

An exemplary method for calibrating a work function of a non-contact voltage sensor is outlined in FIG. 2. Although the method is described below in reference to the components depicted in FIG. 1, the method may be used with any system which utilizes a non-contact voltage sensor to measure voltages of substrates. For example, step 40 of the method references the preparation of a reference sample to have a substantially stable work function. Such a step may be described in reference to components 26 used to substantially stabilize the work function of reference sample 18 in FIG. 1. In other embodiments, however, the components associated with substantially stabilizing the work function of reference sample 18 may be independent of system 10. As such, the method of FIG. 2 may be used in a system with such components included therein or independent of the system. Consequently, although the following description of components 26 is made with reference to being part of system 10, such an inclusion within system 10 is not necessary. In particular, components 26 may or may not be included within system 10.

In general, factors that may affect work function of a substrate or a reference sample may include, but are not limited to, exposure time to ambient environments, surface finish of the sample, and/or the pressure, humidity, temperature, or intensity of illumination within the environment around the sample. As such, several methods and devices may be used to reduce variation in the work function of a reference sample. As noted above, the method to calibrate the work function of a non-contact sensor outlined in FIG. 2 may include step 40 in which a reference sample is prepared to have a substantially stable work function. In general, the reference sample may be prepared in a variety of manners, including any individual or combination of techniques described below. In particular, a reference sample may prepared by any one or more of the techniques described below that are used to treat a reference sample and/or control an environment around a reference sample. As such, the techniques described below in reference to step 40 are neither mutually inclusive nor mutually exclusive.

As stated above, in some embodiments, the preparation of a reference sample, as recited in step 40, may include treating an upper surface of the reference sample. For example, step 40 may include etching an upper surface of reference sample 18 to remove contaminants formed upon the sample. More specifically, step 40 may include exposing reference sample 18 to a stripping solution such as hydrofluoric acid or any other solution used in microelectronic fabrication for stripping surfaces of a topography. Such a treatment process may be particularly advantageous in embodiments in which the upper surface of reference sample 18 includes highly oriented pyrolytic graphite or doped semiconductor materials, as described in more detail below. In addition, such a treatment process may enable reference sample 18 to have a substantially stable work function for a time period between approximately 0.5 seconds and approximately 1000 seconds. In other cases, the preparation of the reference sample in step 40 may additionally or alternatively include forming a layer upon a surface of reference sample 18. In particular, a dielectric or metal film may be formed upon the upper surface of reference sample 18 using deposition techniques known in the fabrication of microelectronic devices. In this manner, reference sample 18 may have a "fresh" surface with which to reference a stable work function of the substrate. In either case, components 26 of system 10 in FIG. 1 may accordingly include any constituent with which to form an additional layer upon reference sample 18 and/or etch an upper surface of reference sample 18. For example, components 26 may include etch and/or deposition solutions as well as a dispensing mechanism with which to introduce such solutions to reference sample 18.

In some embodiments, the preparation of the reference sample in step 40 may additionally or alternatively include controlling the environment around the reference sample. More specifically, step 40 may include manipulating the environment around a reference sample such that the work function of the reference sample does not substantially vary due to exposure to ambient conditions. In other words, step 40 may include isolating reference sample 18 from the ambient environment around substrate 12. In general, several techniques may be used to control the environment around reference sample 18. As such, the techniques used to control the environment about reference sample 18 may generally be referred to herein as environmental parameters with which to isolate reference sample 18. In turn, components 26 may generally include any constituents adapted to control the environment around reference sample 18 and/or treat the upper surface of reference sample 18.

One manner with which to control the environment around reference sample 18 is to surround the sample with a physical barrier. Consequently, components 26 may, in some embodiments, include housing 28 as shown in FIG. 1. In yet other embodiments, however, components 26 may not include housing 28. In particular, the environment around reference sample 18 may be controlled using other techniques or components. For instance, the environment may be additionally or alternatively controlled by purging the environment around the reference sample with one or more gases. In particular, step 40 may include flowing inert gases, such as but not limited to dry air, helium, argon, and/or nitrogen proximate to reference sample 18. In some cases, the flow of gas around reference sample 18 may be continuous. In other embodiments, however, the flow of gas may be periodic. For example, gas flow around reference sample 18 may be for a time period between approximately 0.001 seconds and approximately 1 hour at a frequency between approximately 0.0001 Hz and approximately 1 KHz. Other purge times and frequencies may also be used. In any case, components 26 may include one or more gas nozzles with which to flow gases proximate to the surface of reference sample 18. For example, in an embodiment in which housing 28 is used to surround reference sample 18, components 26 may include gas inlet 30 and gas outlet 32 arranged along the sidewalls of housing 28 as shown in FIG. 1. In some cases, step 40 may include inducing a vacuum about reference sample 18. In such an embodiment, components 26 may further include a pump coupled to gas outlet 32.

In some cases, step 40 may additionally or alternatively include heating and/or cooling the environment around reference sample 18 to control the temperature at which the reference sample is exposed. For example, step 40 may include maintaining the environment around reference sample 18 at a temperature between approximately 20° C. and approximately 1000° C., or more specifically, at a temperature between 300° C. and approximately 1000° C. In some embodiments, temperatures above room temperature may prevent contaminates from adsorbing onto the sample. In any case, the temperature around reference sample 18 may be maintained for a specific period of time in some embodiments. For example, in some cases, the temperature around reference sample 18 may be maintained for a period of time between approximately 1 second and approximately 1 hour. Longer durations of an elevated temperature may advantageously prevent contaminates from adsorbing onto the sample's surface. In any case, components 26 may include devices adapted to control the temperature of reference sample 18. For example, in some embodiments, components 26 may include heating coil 34 wrapped around substrate holder 36 as shown in FIG. 1.

In some embodiments, step 40 may additionally or alternatively include illuminating reference sample 18 to remove airborne molecular contamination from the environment around the reference sample. In particular, components 26 may include an illumination source, such as an infrared light source, a white light source, an ultraviolet light source, for example, to illuminate reference sample 18. Such an illumination source may be a continuous wave light source or a pulsed light source. In addition, the illumination source may be a lamp or a laser source.

Regardless of the technique used to prepare reference sample 18, the surface of reference sample 18 may, in some embodiments, include materials which are known to maintain a substantially stable work function over a particular period of time. For example, reference sample 18 may include materials which are known to maintain a substantially stable work function for up to approximately 1000 seconds. Materials with such capabilities include noble metals, or more specifically, copper, silver, gold, platinum, palladium, and iridium. Other highly stable materials may be included in reference sample as well or alternatively. For example, in some embodiments, reference sample 18 may include highly oriented pyrolytic graphite. In yet other embodiments, reference sample 18 may include doped semiconductor materials, such as but not limited to doped silicon or doped gallium arsenide.

As shown in FIG. 2, the method for calibrating the work function of a non-contact voltage sensor may further include step 42 in which a voltage of the reference sample is measured using a non-contact voltage sensor. Describing such a measurement step in reference to FIG. 1 may include orienting non-contact voltage sensor 22 over reference sample 18. In an embodiment in which housing 28 surrounds reference sample 18, the measurement step may include opening door 38 of housing 28 to allow a line of sight to be established between non-contact voltage sensor 22 and reference sample 18. In some embodiments, substrate holder 34 may be adapted to move up and down as indicated by the bi-directional arrow in FIG. 1. Consequently, reference sample 18 may be brought closer to non-contact voltage sensor 22. In addition or alternatively, non-contact voltage sensor 22 may be adapted to move closer to reference sample 18.

In some cases, substrate holder 34 may be adapted to raise reference sample 18 out of the controlled environment. Consequently, the method of calibrating the work function of a non-contact voltage sensor may, in some embodiments, include removing the reference sample from the controlled environment prior to measuring the voltage of the reference sample. In addition, the method may include returning the reference sample to the controlled environment subsequent to the step of measuring the reference sample to voltage. In this manner, the one or more environmental parameters within the controlled environment may be maintained while the voltage of the reference sample is being measured. In other embodiments, however, one or more of the environmental parameters within the controlled environment may be terminated while the voltage of the reference sample is being measured. More specifically, the flow of purge gas around reference sample 18 may be stopped, heating and/or cooling of reference sample 18 may be terminated, and/or an illumination source directed toward reference sample 18 may be turned off. In such an embodiment, substrate holder 34 may be adapted raise reference sample 18 above housing 28 or may be adapted to retain reference sample 18 within housing 28 during the measurement process.

Turning back to FIG. 2, the method for calibrating the work function of a non-contact voltage sensor may further include step 44 in which a work function correction factor is determined for the non-contact voltage sensor used in step 42. In particular, step 44 includes determining the work function correction factor from the reference sample voltage measured in step 42. In some cases, the work function correction factor may be determined by calculating a difference between the reference sample voltage measured in step 42 and a previously measured voltage of the reference sample. Such a previously measured reference sample may be from a previous calibration of the non-contact voltage sensor. As will be discussed in more detail below in reference to FIG. 3, a method is provided which includes calibrating a work function of a non-contact voltage sensor repeatedly during the measurement of a plurality of substrates. In particular, the method includes measuring the voltages of a plurality of substrates subsequent to calibrating a work function of the non-contact voltage sensor and repeating the step of calibrating after measuring a subset of the plurality of samples. In this manner, the variation of the non-contact voltage sensor work function between substrate measurements may be determined. In such an embodiment, the reference sample is preferably prepared in the same manner prior to each of the calibration voltage measurements such that the work function of the reference sample may be substantially stable.

In some embodiments, the work function correction factor may be determined by calculating the actual value of the non-contact voltage sensor work function. In particular, the work function of the non-contact voltage sensor may be calculated from a known work function of the reference sample and preset voltage values of the reference sample and the non-contact voltage sensor. More specifically, the reference sample and non-contact voltage sensor may be biased with a known voltage between approximately −200 volts and approximately 200 volts, for example. Larger or smaller bias voltages may be used, however, depending on the design specifications of the system. In addition, the work function of the reference sample may be predetermined by equating two measurements of the reference sample and canceling out the affect of the non-contact voltage sensor work function. Once the work function of the reference sample and preset voltage values of the reference sample and the non-contact voltage sensor are known, the variation of the non-contact voltage sensor work function may be tracked and calibrated.

Figure 3:
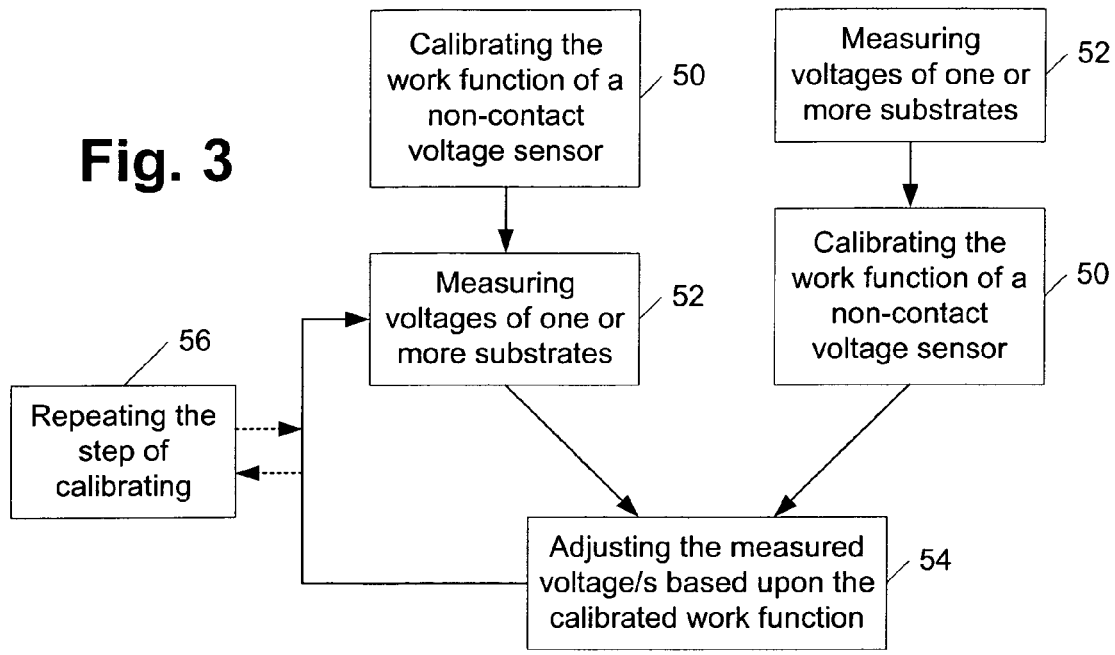
FIG. 3 depicts a flowchart of a method for measuring electrical properties of a substrate using a non-contact voltage sensor.

In either case, the calibrated work function of the non-contact voltage sensor may be used to adjust the voltage measurement of substrate 12. A method for measuring one or more substrates using a non-contact voltage sensor system is outlined in FIG. 3. In particular, FIG. 3 shows the method including steps 50 and 52 in which the work function of a non-contact voltage sensor is calibrated and voltages of one or more substrates are measured, respectively. In addition, the method includes adjusting the measured substrate voltages based upon the calibrated work function as shown in step 54. In some embodiments, the adjustment process of step 54 may include subtracting the calibrated work function from the one or more measured substrate voltages. In yet other embodiments, the adjustment process of step 54 may be included within step 52 of measuring the one or more voltages. More specifically, the adjustment process may include reconfiguring the non-contact voltage sensor to automatically accommodate the work function correction factor that was determined in the calibration step. In any case, step 54 may include adjusting any type of voltage measurement, including but not limited to surface voltage measurements, flatband voltage measurements, and/or tunneling voltage measurements.

In either case, the method may include having step 50 conducted prior to step 52 or vice versa, as shown in FIG. 3. In particular, the method may first include calibrating the work function of a non-contact voltage sensor and then measuring and adjusting measured voltages of one or more substrates based upon the calibrated work function of the non-contact voltage sensor. In yet other embodiments, the method may first include measuring the voltages of one or more substrates and then calibrating the work function of the non-contact voltage sensor. In such an embodiment, the method may include a feedback process such that the one or more measured substrate voltages can be adjusted based upon the calibrated work function of the non-contact voltage sensor. In either case, the method may continue to measure voltages of one or more substrates and adjusting the measured voltages based upon the calibrated work function as shown in the feedback loop between steps 54 and 52. In some cases, the feedback loop may include step 56 in which the step of calibrating is repeated. Such a repeating step may be conducted after measuring a subset of a plurality of samples. In some cases, step 56 may be conducted between each voltage measurement of the plurality of samples. In other embodiments, however, step 56 may be conducted after measuring the voltage of more than one sample.

In general, electrical properties of the substrates may be determined from the adjusted voltage measurements determined in step 54. For example, electrical properties such as capacitance, dielectric constant, and/or thickness of the substrates may be determined from the adjusted voltage measurements. In addition or alternatively, the method may include tracking the adjusted voltage measurements such that process parameters of a fabrication process may be maintained within specification. In response, parameters of process tools may be adjusted using feedback or feedforward control techniques. More specifically, parameters of process tools used earlier in the process may be altered or parameters of process tools used for further processing of the substrate may be altered based upon the adjusted voltage measurements.

As stated above, exemplary configurations of corona discharge guns are illustrated in FIGS. 4a–6. In fact, several different component configurations and arrangements, which are not necessarily mutually inclusive, are discussed in reference to the corona guns depicted in FIGS. 4a–6. Consequently, the corona guns provided herein are not restricted to the combination of component configurations illustrated in FIGS. 4a–6. Rather, a corona gun, as described herein, may include any number of the component configurations described in reference to any of the illustrations included within FIGS. 4a–6. More specifically, the corona gun provided herein may include needles and/or wires arranged parallel, orthogonal, or at an angle relative to a sidewall of a beam shaping electrode of the corona gun as described in more detail below. In addition or alternatively, the corona gun provided herein may include beam shaping electrodes arranged inset within each other and/or may be adapted to move relative to each other as described in reference to FIGS. 5a and 6.

Figure 4A:
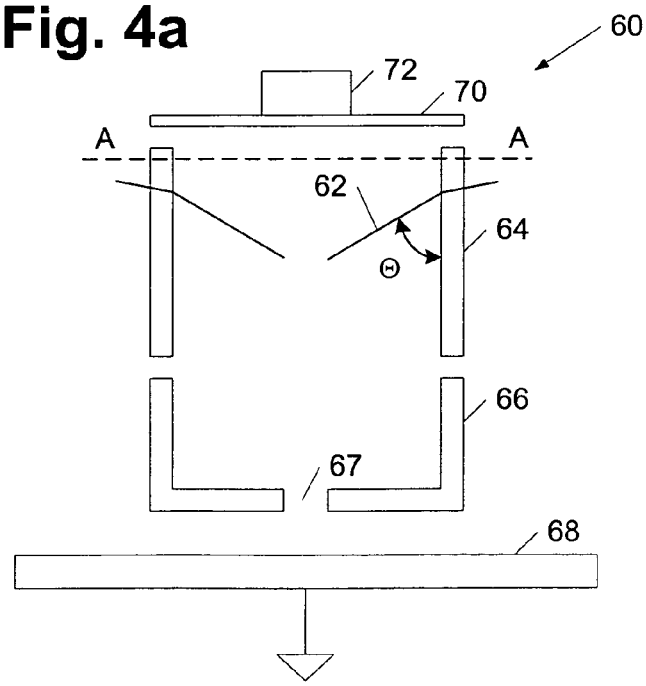
FIG. 4a depicts a partial cross-sectional view of a corona gun.

FIG. 4a illustrates a partial cross-sectional view of corona gun 60 with beam shaping electrodes 64 and 66. In general, electrodes 64 and 66 may be used to guide corona ions through corona gun 60 to an underlying specimen, such as substrate 68. More specifically, beam shaping electrode 64 may be used for first order correction of the corona pattern generated within corona gun 60, while beam shaping electrode 66 may be used for second order correction of the corona pattern. In other words, beam shaping electrode 64 may be used to converge the corona ions generated within corona gun 60 into a trajectory having dimensions substantially similar to the area surrounded by beam shaping electrode 64. Beam shaping electrode 66, on the other hand, may include opening 67 to further converge the ions onto an area of interest on substrate 68. In some cases, the portions of beam shaping electrode 66 forming the lateral boundaries of opening 67 may be substantially straight and vertical as shown in FIG. 4a. In other embodiments, however, the portions of beam shaping electrode 66 forming the lateral boundaries of opening 67 may be rounded and/or tapered. An exemplary beam shaping electrode with such an opening is described in more detail below in reference to FIG. 5a. In either case, however, the width of opening 67 may be between approximately 5 µm and approximately 4 cm. In addition, opening 67 may be configured into any shape, including but not limited to a circle, square, or rectangle.

In general, beam shaping electrodes 64 and 66 may be maintained at known electrical potentials. In some embodiments, electrodes 64 and 66 may be maintained at a substantially the same voltage. In other embodiments, however, electrodes 64 and 66 may be maintained at different voltages. In either case, beam shaping electrode 64 may be biased to a potential between 0 volts and approximately 5000 volts. In contrast, beam shaping electrode 66 may be biased to a potential between 0 volts and approximately 1000 volts. Larger potentials, however, may be used for electrodes 64 and/or 66, depending on the process parameters of the corona deposition process. In any case, substrate 68 may be grounded as shown in FIG. 4a. Substrate 68 may include similar configurations and materials as those described in reference to substrate 12 and reference sample 18 in FIG. 1.

In general, beam shaping electrodes 64 and 66 may be spaced apart and coupled together by insulating materials. In particular, beam shaping electrode 64 and 66 may be spaced apart by a distance which is sufficient to avoid arcing between the electrodes. Such a distance may generally be between approximately 0.2 inches and approximately 1 inch, however, larger or smaller distances may be used, depending on the design specifications of the corona gun. In some cases, beam shaping electrode 64 and 66 may have substantially similar inner widths and, therefore, may be arranged in alignment with each other as shown in FIG. 4a. In other embodiments, however, beam shaping electrodes 64 and 66 may not have similar inner widths and, therefore, in some cases, may be inset within each other. An exemplary corona gun with an inset configuration is described in more detail below in reference to FIG. 5a. In yet other embodiments, beam shaping electrodes 64 and 66 may have different inner widths, but may not be inset within each other.

In any case, beam shaping electrodes 64 and 66 may include inner widths between approximately 0.5 inches and approximately 3.0 inches, depending on the design characteristics of the corona gun. In addition, beam shaping electrodes 64 and 66 may be formed into any cylindrical shape, including shapes adapted to surround spaces with rounded or straight edges. Moreover, the lengths of beam shaping electrodes 64 and 66 may be substantially similar or may be substantially different. In particular, beam shaping electrode 64 may have a length between approximately 1 inch and approximately 5 inches. In some cases, the length of beam electrode 64 may be particularly configured to create a distance of approximately 0.25 inches and approximately 4.0 inches between the corona excitation sources of conductive rods 62 and beam shaping electrode 66. In contrast, beam shaping electrode 66 may have a length between approximately 0.2 inches and approximately 2 inches. Electrodes 64 and/or 66 may have larger or smaller lengths, however, depending on the design characteristics of the corona gun. For example, beam shaping electrodes 64 and/or 66 may be particularly configured to space substrate 68 from beam shaping electrode 64 at a distance between approximately 20 µm and approximately 1 cm.

In some embodiments, corona gun 60 may include an additional beam shaping electrode spaced between beam shaping electrode 66 and substrate 68. An exemplary corona gun with such an additional beam shaping electrode is described in reference to FIG. 5a below. In some embodiments, corona gun 60 may further include cover 70 and/or environmental control device 72 as shown in FIG. 4a. In yet other embodiments, cover 70 and/or environmental control device 72 may be omitted from corona gun 60. In general, cover 70 may serve to prevent corona ions from discharging out of the top end of corona gun 60. Environmental control device 72, on the other hand, may serve a variety of different purposes. For example, environmental control device 72 may include a light source with which to illuminate substrate 68 prior to, during or subsequent to the deposition of corona ions. In addition or alternatively, environmental control device 72 may include one or more gas inlets and outlets to allow gases to be introduced and exhausted from corona gun 60. In other cases, gases may be additionally or alternatively introduced and/or exhausted from corona gun 60 by gas inlets and outlets arranged along other portions of the corona gun. In any case, gases may be introduced into corona gun 60 to assist in the delivery of charge through corona gun 60 to an underlying specimen. Such gases may include, but are not limited to air, helium, nitrogen, and/or carbon dioxide.

In addition to the aforementioned components, corona gun 60 may further include conductive rods 62 as shown in FIG. 4a. In general, conductive rods 62 may be biased to a relatively high voltage source during operation of corona gun 60 such that conductive rods 62 may serve as a corona excitation source. For example, in some embodiments, conductive rods 62 may be biased to have a potential between approximately 1000 volts and approximately 15,000 volts. Larger or smaller voltage biases, however, may be used for conductive rods 62, depending on the design specifications of the device and the process parameters of the corona deposition process. In any case, conductive rods 62 may include a material which is relatively stable and substantially inert to reactions with corona generated species. In particular, the material of the conductive rods 62 may be selected such that the material may not dissociate under the field in which the corona is generated. Examples of appropriate materials for conductive rods 62 include, but are not limited to, tungsten, gold, silver, copper, steel, platinum, or any alloys of such materials. In some embodiments, conductive rods 62 may include semi-conductive materials, such as silicon or germanium, for example.

As shown in FIG. 4a, conductive rods 62 may extend into a space surrounded by beam shaping electrode 64. In particular, conductive rods 62 may be arranged at an angle between approximately 0 degrees and approximately 90 degrees with respect to the sidewall of beam shaping electrode 64 as noted by angle $\Theta$. In some embodiments, conductive rods 62 may be arranged at substantially the same angle relative to the sidewalls of beam shaping electrode 64. In yet other embodiments, however, conductive rods 62 may be arranged at different angles with respect to the sidewalls of a beam shaping electrode. In either case, the angling of conductive rods 62 may advantageously increase the current density of corona charge through corona gun 60 relative to a configuration in which conductive rods 62 are arranged orthogonal to the sidewalls of beam shaping electrode 64. As a result, the deposition rate of the corona charge onto substrate 68 may increase as angle $\Theta$ decreases. In addition, the angling of conductive rods 62 may advantageously provide more stable current levels within corona gun 60 relative to a configuration in which conductive rods 62 are arranged parallel to the sidewalls of beam shaping electrode 64. As a result, corona charge may be deposited in a more uniform manner as angle $\Theta$ increases. In some embodiments, the angle of conductive rods 62 relative to the sidewalls of beam shaping electrode 64 may be optimized to deposit corona charge in a manner which meets the uniformity and efficiency objectives of the deposition process.

In general, the configuration of conductive rods 62 may be in the form of wires and/or needles. "Needles", as used herein, may refer to conductive rods which are supported at one end and suspended at the other end. For example, conductive rods 62 in FIG. 4a are depicted as needles, having one end supported at the sidewalls of beam shaping electrode 64 and the other end suspended within the space surrounded by beam shaping electrode 64. In an alternative embodiment, conductive rods 62 may include needles having one end supported by cover 70 or a different supporting member arranged above corona gun 60. In contrast, "wires", as used herein, may refer to conductive rods which are supported at both ends. An exemplary configuration of a corona gun having wires extending between sidewalls of a beam shaping electrode is shown in FIG. 5a and described in more detail below.

Figure 4B:
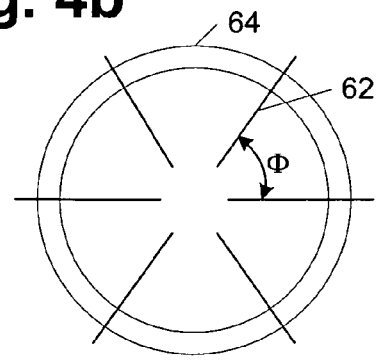

In an embodiment in which conductive rods 62 includes a plurality of needles, the plurality of needles may, in some cases, be concentrically spaced from each other by less than approximately 90 degrees as shown in FIG. 4b. In particular, FIG. 4b illustrates a top view of corona gun 60 taken along line AA of FIG. 4a. As shown in FIG. 4b, conductive rods 62 may be concentrically separated by angle $\phi$, which may be less than approximately 90 degrees when corona gun 60 includes more than four conductive rods uniformly spaced from each other. In other cases, however, conductive rods 62 may not be uniformly spaced from each other. In such an embodiment, at least two conductive rods may be spaced apart by less than approximately 90 degree. Consequently, corona gun 60 may, in some embodiments, include less than, more than, or exactly four conductive rods which are concentrically spaced from each other by less than approximately 90 degrees.

It is noted that the configuration of having a plurality of conductive rods concentrically spaced from each other by less than approximately 90 degrees and the configuration of having conductive rods arranged at an angle between approximately 0 degrees and approximately 90 degrees with respect to the sidewall of beam shaping electrode is not necessarily mutually inclusive. In particular, the corona gun provided herein may include conductive rods arranged parallel and/or orthogonal to a sidewall of a beam shaping electrode in addition to or alternative to the conductive rods arranged at an angle with respect of the beam shaping electrode sidewall. In addition, conductive rods 62 may, in some embodiments, be in the form of wires and, therefore, may not be arranged concentrically within an area surrounded by beam shaping electrode 64. Furthermore, although corona gun 60 is shown to include two conductive rods arranged, the corona gun described herein are not restricted to such a number or arrangement of conductive rods. In particular, the corona gun described herein may generally include any number of conductive rods. For example, the corona gun described herein may include between one and eight conductive rods in some embodiments. In other cases, however, the corona gun provided herein may include more than eight conductive rods.

Figure 5A:
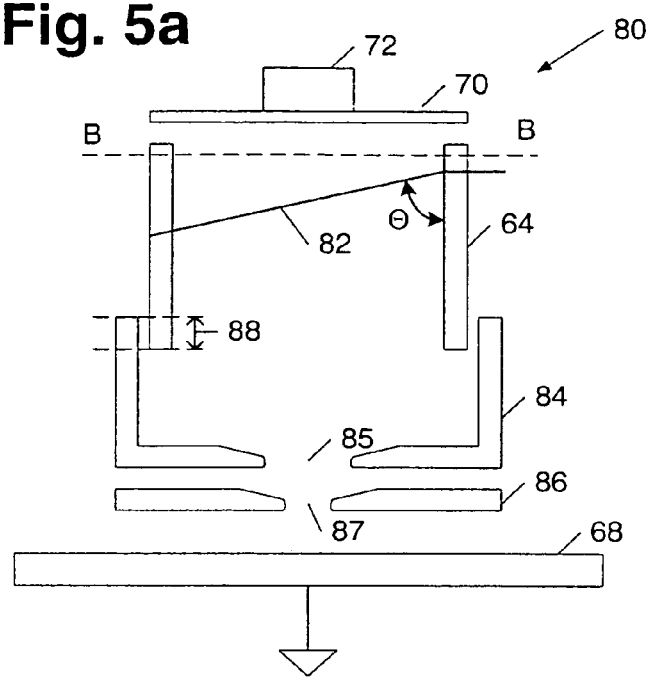
FIG. 5a depicts a partial cross-sectional view of a corona gun in an alternative embodiment.

A different configuration of a corona gun is illustrated in FIG. 5a. In particular, FIG. 5a illustrates corona gun 80 having two beam shaping electrodes inset within each other and an additional beam shaping electrode interposed between the inset beam shaping electrodes and an underlying substrate as is described in more detail below. In addition, FIG. 5a illustrates corona gun 80 with a wire for a corona excitation source. In particular, corona discharge gun 80 may include conductive rod 82 extending between sidewalls of beam shaping electrode 64 and therefore, is illustrated as a wire. In other embodiments, however, conductive rod 82 may alternatively be configured as a needle.

Figure 5B:
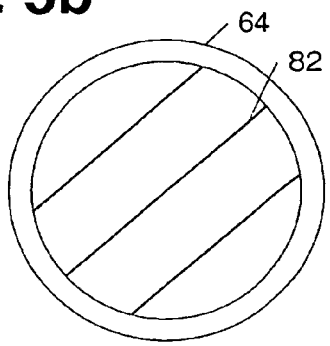

In either case, conductive rod 82 may be arranged at an angle between approximately 0 degrees and approximately 90 degrees with respect to the sidewall of beam shaping electrode 64, as shown by angle $\Theta$ in FIG. 5a. In some embodiments, corona gun 80 may include a plurality of conductive rods arranged at such an angle. For example, corona gun 80 may include a plurality of wires arranged parallel to each other and spaced apart by an amount between approximately 1 mm and approximately 5 mm. In a preferred embodiment, the ends of the wires may be supported at substantially the same elevational position along beam shaping electrode 64 such that the wires are arranged within same plane. A top view of corona gun 80 having such a configuration of wires is illustrated in FIG. 5b. In particular, FIG. 5b illustrates a top view of corona gun 80 taken along line BB in FIG. 5a. Although FIG. 5b shows corona gun 80 having three wires, corona gun 80 may include any number of wires, including wires arranged in parallel and in the plane of the wires depicted in FIG. 5b as well as any wires arranged above or below such a plane of wires. In a preferred embodiment, the number of wires included within corona gun 80 may range from one to four, however, corona gun 80 is not restricted to such a quantity.

In general, corona gun 80 may include beam shaping electrode 64 having substantially similar dimensional characteristics as electrode 64 in FIG. 4a. In addition, corona gun 80 may include top 70 and/or environmental control device 72 serving similar roles as described in reference to corona gun 60 in FIG. 4a. In yet other embodiments, cover 70 and/or environmental control device 72 may be omitted from corona gun 80. In any case, corona gun 80 may include beam shaping electrode 84 spaced adjacent to beam shaping electrode 64 as shown in FIG. 5a. Similar to beam shaping electrode 66 in FIG. 4a, beam shaping electrode 84 may provide a second order of correction of a corona pattern generated within corona gun 80. In general, beam shaping electrode 84 may include similar dimensional characteristics as beam shaping electrode 66 of corona gun 60. In the configuration of corona gun 80, however, beam shaping electrode 84 preferably includes an inner width which is larger than an outer width of beam shaping electrode 64. In this manner, beam shaping electrode 64 may be inset within beam shaping electrode 84. Alternatively, beam shaping electrode 84 may have an outer width which is smaller than an inner width of beam shaping electrode 64. In such an embodiment, beam shaping electrode 84 may be inset within beam shaping electrode 64. In either case, beam shaping electrode 84 may be arranged such that a portion of the electrode overlaps beam shaping electrode 64. In some cases, beam shaping electrode 84 may be inset at least approximately 0.1 inches into the space surrounded by the beam shaping electrode 64.

An overlap configuration between beam shaping electrodes 64 and 86 may advantageously minimize the area of exposed dielectric surfaces of the insulating material used to couple the electrodes. In general, the area of exposed dielectric surface between two beam shaping electrodes may be governed by the area between the electrodes. In an embodiment in which a portion of beam shaping electrode 84 overlaps beam shaping electrode 64, the area may be governed by the difference between the inner width of electrode 84 and the outer width of electrode 64. Such a dimension is referenced as numeral 88 in FIG. 5a and may, generally, be between approximately 0.2 inches and approximately 1 inch. However, electrodes 64 and 84 may be spaced apart by larger or smaller amounts, depending on the design specifications of the corona gun.

In some cases, corona source 80 may further include beam shaping electrode 86 interposed between beam shaping electrode 84 and substrate 68. In general, beam shaping electrode 86 may be spaced apart from beam shaping electrode 84 by an amount between approximately 0.2 inches and approximately 1.0 to avoid arcing between the electrodes. In addition, substrate 68 may be spaced apart from beam shaping electrode 86 by an amount between approximately 20 μm and approximately 1 cm. In some cases, beam shaping electrode 86 may be biased at a substantially similar potential as beam shaping electrode 84. In other embodiments, beam shaping electrode 86 may be biased at a different potential than beam shaping electrode 84. In any case, beam shaping electrodes 84 and 86 may generally be biased at a potential between approximately 0 volts and approximately 1000 volts. Alternatively, beam shaping electrode 86 may be omitted from corona gun 80.

As shown in FIG. 5a, beam shaping electrodes 84 and 86 may include openings 85 and 87, respectively. The openings may be used to focus the corona ions generated within corona gun 80 onto a specified area of substrate 68. In general, at least one of openings 85 and 87 may include a width between approximately 5 microns and approximately 4 cm. In some embodiments, openings 85 and 87 may have substantially similar widths. In yet other embodiments and as shown in FIG. 5a, opening 87 may be smaller than opening 85. Consequently, beam shaping electrode 86 may be the lowest aperture of corona gun 80 in some embodiments. In some embodiments, at least one of openings 85 and 87 may be tapered as shown in FIG. 5a. In particular, at least one of openings 85 and 87 may be tapered at an angle between approximately 10 degrees and approximately 90 degrees. Such a tapering of openings 85 and 87 may increase the exposure area of the respective beam shaping electrodes, increasing the current density and, therefore, the deposition rate of the corona gun.

In addition or alternatively, portions of at least one of beam shaping electrodes 84 and 86 forming the lateral boundaries of openings 85 and 87 may be rounded as shown in FIG. 5a. Rounding of such a portion of a beam shaping electrode may advantageously prevent an electrical discharge spot from forming around the opening of the electrode when a bias voltage is applied. In yet other embodiments, the portions beam shaping electrodes 84 and 86 forming the lateral boundaries of openings 85 and 87, respectively, may not be tapered and/or rounded. Rather, beam shaping electrodes 84 and/or 86 may have a substantially straight and vertical profile bordering their respective openings. In particular, the portions beam shaping electrodes 84 and 86 forming the lateral boundaries of openings 85 and 87 may have a profile similar to the profile shown and described in reference to beam shaping electrode 66 in FIG. 1.

Figure 6:
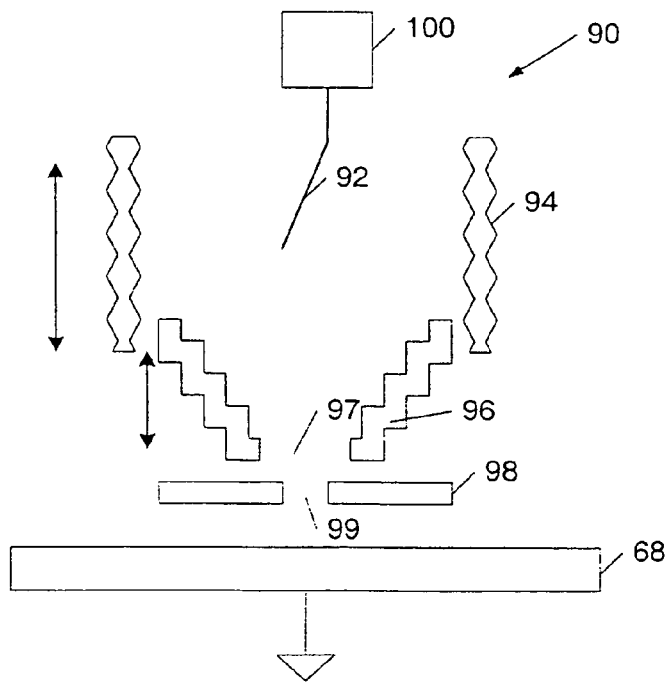
FIG. 6 depicts a partial cross-sectional view of a corona gun in yet another alternative embodiment.

In any case, the corona gun described herein may additionally or alternatively be configured to alter the length of the gun, or more specifically, the distance between a corona excitation source and an opening of a beam shaping electrode. An exemplary configuration of a corona gun offering several manners with which to accommodate such a length altering adaptation is illustrated in FIG. 6. In particular, FIG. 6 illustrates corona gun 90 including conductive rod 92 (i.e., corona excitation source 92) and beam shaping electrodes 94, 96, and 98 configured to alter the distance between the distal end of conductive rod 92 and opening 99 of beam shaping electrode 98. In an embodiment in which beam shaping electrode 98 is omitted from corona gun 90, the components of corona gun 90 may alternatively be configured to alter the distance between the distal end of conductive rod 92 and opening 97 of beam shaping electrode 96.

As shown in FIG. 6, conductive rod 92 may, in some embodiments, be suspended from component 100. In general, component 100 may be arranged above beam shaping electrode 94 to suspend conductive rod 92 within the space surrounded by the electrode. In some cases, component 100 may be adapted to raise and lower conductive rod 92 relative to the position of beam shaping electrode 94. In particular, component 100 may be adapted to position the distal end of conductive rod 92 relative to an upper surface of beam shaping electrode 94. For example, in some embodiments, conductive rod 92 may be positioned to have its distal end extending below the upper surface of beam shaping electrode 94 by an amount between approximately 1 inch and approximately 4 inches. Although corona gun 90 does not illustrate the inclusion of top 70 and environmental control device 72, the configuration of corona gun 90 is not restricted to the exclusion or inclusion of such components.

As noted above, beam shaping electrodes 94 and/or 96 may, in some embodiments, be configured to alter the distance between the distal end of conductive rod 92 and opening 99 of beam shaping electrode 98. In particular, beam shaping electrodes 94 and/or 96 may be configured to contract and expand. For example, one or both of beam shaping electrodes 94 and 96 may include accordion-style sidewalls as shown for electrode 94 in FIG. 6. With such a configuration, the sidewalls of the beam shaping electrode may be configured to fold into itself. In addition or alternatively, one or both of beam shaping electrodes 94 and 96 may include telescoped sidewalls as shown for electrode 96 in FIG. 6. In such an embodiment, portions of the sidewalls may be configured to nest into each other. In yet other cases, beam shaping electrodes 94 and 96 may be additionally or alternatively configured to move relative to each other. More specifically, beam shaping electrodes 94 and 96 may be configured to telescope into each other. In yet other embodiments, beam shaping electrode 98 may be configured to move relative to beam shaping electrode 96. In particular, beam shaping electrode 98 may be configured to move closer or farther away from beam shaping electrode 96. In any case, substrate 68 may also be configured to move to maintain a desired distance from nearest beam shaping electrode of corona gun 90.

It will be appreciated to those skilled in the art having the benefit of this disclosure that this invention is believed to provide a system and method for calibrating the work function of a non-contact voltage sensor as well as different configurations of corona discharge guns. Further modifications and alternative embodiments of various aspects of the invention will be apparent to those skilled in the art in view of this description. For example, the methods and systems may be used with any type of non-contact voltage sensor, including but not limited to Kelvin probes, Monroe probes, or atomic force microscope probes. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A corona discharge system, comprising:
a first beam shaping electrode; and
one or more conductive rods extending into a space surrounded by the first beam shaping electrode, wherein the one or more conductive rods are respectively arranged at angles greater than approximately 0 degrees and less than approximately 90 degrees with respect to a sidewall of the first beam shaping electrode.

2. The corona discharge system of claim 1, wherein the one or more conductive rods comprise a plurality of needles suspended within the space surrounded by the first beam shaping electrode and concentrically spaced from each other by less than approximately 90 degrees.

3. The corona discharge system of claim 1, wherein the one or more conductive rods comprise a plurality of wires extending between sidewalls of the first beam shaping electrode, wherein the plurality of wires are arranged parallel to each other and spaced apart by an amount between approximately 1 mm and approximately 5 mm.

4. The corona discharge gun of claim 1, wherein the conductive rod is one of more than four conductive rods.

5. The corona discharge system of claim 1, further comprising a second beam shaping electrode spaced adjacent to the first beam shaping electrode, wherein a portion of the second beam shaping electrode overlaps a portion of the first beam shaping electrode.

6. A corona discharge gun comprising a plurality of needles concentrically arranged less than approximately 90 degrees from each other.

7. The corona discharge gun of claim 6, wherein the plurality of needles comprises more than four needles.

8. The corona discharge gun of claim 6, further comprising a first beam shaping electrode surrounding the plurality of needles, wherein at least one of the plurality of needles is angled between approximately 0 degrees and approximately 90 degrees with respect to a sidewall of the first beam shaping electrode.

9. The corona discharge gun of claim 8, further comprising
a second beam shaping electrode spaced adjacent to the first beam shaping electrode; and
a third beam shaping electrode spaced adjacent to the second beam shaping electrode.

10. The corona discharge system of claim 9, wherein at least one of the second and third beam shaping electrodes comprises an opening having a width between approximately 5 microns and approximately 4 cm.

11. The corona discharge system of claim 9, wherein at least one of the second and third beam shaping electrodes comprises a tapered opening.

12. The corona discharge system of claim 9, wherein at least one of the second and third beam shaping electrodes comprises an opening, and wherein portions of the at least one beam shaping electrode forming the lateral boundaries of the opening are rounded.

13. A device adapted to discharge a corona charge, comprising:
a first beam shaping electrode; and
a second beam shaping electrode at least partially inset within a space surrounded by the first beam shaping electrode.

14. The device of claim 13, wherein the second beam shaping electrode is inset at least approximately 0.1 inches into the space surrounded by the first beam shaping electrode.

15. The device of claim 13, wherein a portion of the second beam shaping electrode inset within the space surrounded by the first beam shaping electrode is configured to surround a space having a width which is approximately 0.2 inches to approximately 1.0 inch smaller than a width of the space surrounded by the first beam shaping electrode.

16. The device of claim 13, further comprising a conductive rod suspended within the space surrounded by the first beam shaping electrode.

17. The device of claim 13, further comprising a conductive rod suspended within a space surrounded by the second beam shaping electrode.

18. A corona discharge gun, comprising:
a corona excitation source; and
a first beam shaping electrode adapted to guide and discharge corona charged ions through an opening within the first beam shaping electrode, wherein the corona discharge gun is adapted to have a distance between the corona excitation source and the opening altered.

19. The corona discharge gun of claim 18, wherein the first beam shaping electrode is adapted to contract and expand.

20. The corona discharge gun of claim 19, wherein the first beam shaping electrode comprises telescoped sidewalls.

21. The corona discharge gun of claim 19, wherein the first beam shaping electrode comprises accordion-style sidewalls.

22. The corona discharge gun of claim 18, further comprising a second beam shaping electrode interposed between the corona excitation source and the first beam shaping electrode.

23. The corona discharge gun, of claim 22, wherein at least one of the first and second beam shaping electrodes is adapted to move relative to the other.

24. The corona discharge gun of claim 22, wherein the corona excitation is suspended within the second beam shaping electrode and is configured to move relative to an end of the second beam shaping electrode.

* * * * *